(12) United States Patent
Neumann et al.

(10) Patent No.: US 10,974,646 B2
(45) Date of Patent: Apr. 13, 2021

(54) METHOD FOR OPERATING A MOTOR VEHICLE AND MOTOR VEHICLE

(71) Applicant: Daimler AG, Suttgart (DE)

(72) Inventors: Marcus Neumann, Stuttgart (DE); Gudrun Schoenherr, Holzgerlingen (DE); Thomas Siegel, Ludwigsburg (DE)

(73) Assignee: Daimler AG, Stuttgart (DE)

( * ) Notice: Subject to any disclaimer, the term of this patent is extended or adjusted under 35 U.S.C. 154(b) by 0 days.

(21) Appl. No.: 16/310,226

(22) PCT Filed: Jun. 1, 2017

(86) PCT No.: PCT/EP2017/000644
§ 371 (c)(1),
(2) Date: Dec. 14, 2018

(87) PCT Pub. No.: WO2017/215781
PCT Pub. Date: Dec. 21, 2017

(65) Prior Publication Data
US 2019/0322213 A1    Oct. 24, 2019

(30) Foreign Application Priority Data

Jun. 15, 2016    (DE) .................... 10 2016 007 272.5

(51) Int. Cl.
*B60Q 9/00*    (2006.01)
*A61B 5/024*    (2006.01)
(Continued)

(52) U.S. Cl.
CPC ............... *B60Q 9/00* (2013.01); *A61B 5/024* (2013.01); *A61B 5/0816* (2013.01); *A61B 5/18* (2013.01);
(Continued)

(58) Field of Classification Search
CPC ......... B60Q 9/00; A61B 5/024; A61B 5/0816; A61B 5/18; A61B 5/746; A61M 21/02;
(Continued)

(56) References Cited

U.S. PATENT DOCUMENTS

| 4,641,345 A | 2/1987 | Takahashi |
| 8,140,344 B2 | 3/2012 | Kameyama |

(Continued)

FOREIGN PATENT DOCUMENTS

| DE | 10 2006 015 332 A1 | 11/2006 |
| DE | 10 2010 056 397 A1 | 6/2012 |

(Continued)

OTHER PUBLICATIONS

PCT/EP2017/000644, International Search Report dated Aug. 17, 2017 (Two (2) pages).

(Continued)

*Primary Examiner* — Hung T Nguyen
(74) *Attorney, Agent, or Firm* — Crowell & Moring LLP

(57) ABSTRACT

A method for operating a motor vehicle having a seat arranged in an interior of the motor vehicle for a passenger, into which seat at least one oscillator for transmitting oscillations to the passenger's body is integrated, and having a sound system for acoustic sound reproduction in the interior, includes determining the passenger's passenger state and selecting and reproducing a type of a sound sequence that is associated with the passenger's state via the sound system. The at least one such oscillator is activated on the basis of the selected type of sound sequence. In this way, convenience functions and/or assistance systems of the motor vehicle can be improved.

13 Claims, 1 Drawing Sheet

(51) Int. Cl.
  *A61B 5/08* (2006.01)
  *A61B 5/18* (2006.01)
  *A61M 21/02* (2006.01)
  *B60H 3/00* (2006.01)
  *B60W 40/09* (2012.01)
  *B60W 50/16* (2020.01)
  *A61B 5/01* (2006.01)
  *A61B 5/021* (2006.01)
  *A61B 5/145* (2006.01)
  *A61M 21/00* (2006.01)

(52) U.S. Cl.
  CPC ........... *A61M 21/02* (2013.01); *B60H 3/0007* (2013.01); *B60W 40/09* (2013.01); *B60W 50/16* (2013.01); *A61B 5/01* (2013.01); *A61B 5/021* (2013.01); *A61B 5/02405* (2013.01); *A61B 5/14532* (2013.01); *A61M 2021/0016* (2013.01); *A61M 2021/0027* (2013.01); *A61M 2021/0044* (2013.01); *A61M 2230/04* (2013.01); *A61M 2230/201* (2013.01); *A61M 2230/30* (2013.01); *A61M 2230/42* (2013.01); *A61M 2230/50* (2013.01); *B60W 2540/22* (2013.01); *B60W 2540/30* (2013.01); *B60W 2555/20* (2020.02)

(58) Field of Classification Search
  CPC ..... G06Q 30/00; B60H 3/0007; B60W 40/09; B60W 50/16; B60W 40/08; B60W 2540/22; B60K 28/066; G08B 21/06; G06K 9/00845; G06K 2009/00939
  USPC ....... 340/438, 439; 382/104, 182; 705/1, 15, 705/26; 701/1, 36
  See application file for complete search history.

(56) References Cited

U.S. PATENT DOCUMENTS

| | | | |
|---|---|---|---|
| 8,698,639 B2* | 4/2014 | Fung | B60K 28/06 340/576 |
| 8,930,086 B2 | 1/2015 | Khanafer et al. | |
| 9,539,944 B2* | 1/2017 | Tzirkel-Hancock | B60Q 9/00 |
| 9,682,622 B2* | 6/2017 | Kim | B60W 40/08 |
| 9,855,956 B2* | 1/2018 | Omi | B60W 30/12 |
| 9,977,239 B2* | 5/2018 | Muramatsu | G02B 27/0101 |
| 10,189,434 B1* | 1/2019 | Casaburo | B60Q 9/00 |
| 2006/0235753 A1* | 10/2006 | Kameyama | B60H 1/00742 705/15 |
| 2007/0257529 A1 | 11/2007 | Matsuhashi | |
| 2008/0311983 A1 | 12/2008 | Koempel et al. | |
| 2016/0001781 A1* | 1/2016 | Fung | G16H 50/20 701/36 |

FOREIGN PATENT DOCUMENTS

| | | |
|---|---|---|
| DE | 10 2012 013 549 A1 | 1/2013 |
| DE | 10 2012 020 901 A1 | 4/2014 |
| FR | 2 998 159 A1 | 5/2014 |
| GB | 2 170 666 A | 8/1986 |
| JP | 2004-328214 A | 11/2004 |
| JP | 2006-102362 A | 4/2006 |
| JP | 2007-145226 A | 6/2007 |
| WO | WO 2014/149657 A1 | 9/2014 |

OTHER PUBLICATIONS

German Office Action issued in German counterpart application No. 10 2016 007 272.5 dated Dec. 31, 2018 (Six (6) pages).

Japanese Office Action issued in Japanese application No. 2018-564406 dated Nov. 19, 2019, with partial English translation (Seven (7) pages).

* cited by examiner

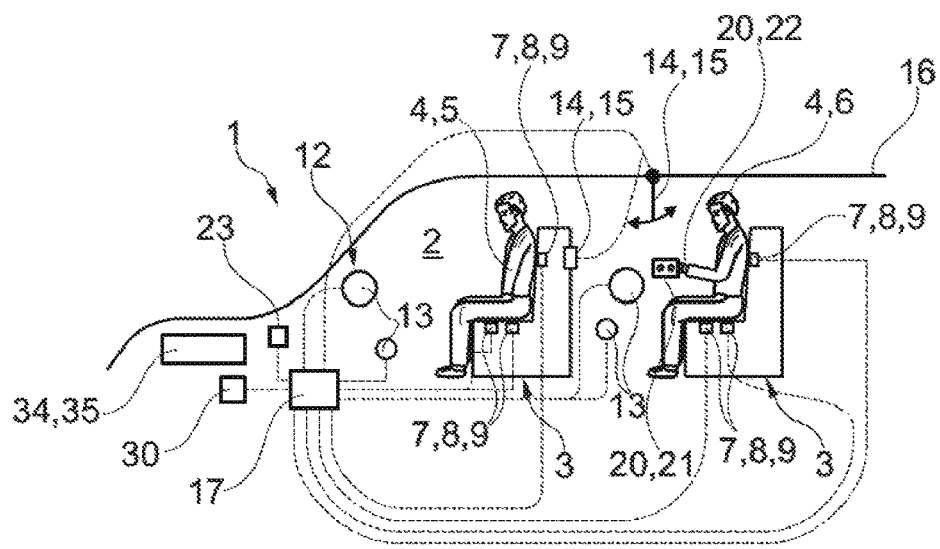
Fig. 1
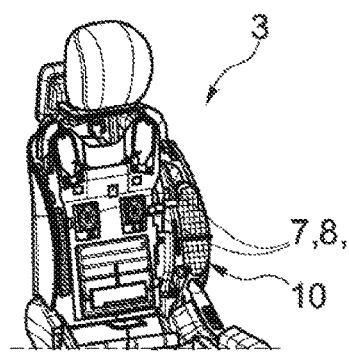
Fig. 2
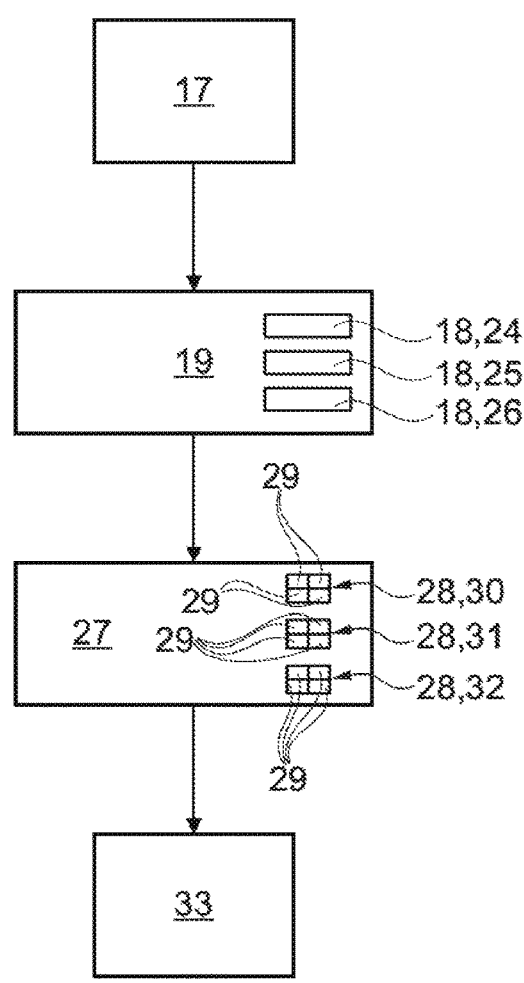
Fig. 3
Fig. 4

METHOD FOR OPERATING A MOTOR VEHICLE AND MOTOR VEHICLE

BACKGROUND AND SUMMARY OF THE INVENTION

The present invention relates to a method for operating a motor vehicle having a seat, a seat-integrated oscillator and a sound system. The invention further relates to such a motor vehicle.

Comfort functions for passengers, in particular for a driver, of a motor vehicle and passenger-assisting assistance systems are becoming increasingly important. Such comfort systems include, for example, a massage function integrated in a seat for a passenger of the motor vehicle, which usually is composed of an oscillation unit in the seat. Assistance systems include, in particular, safety-enhancing devices as well as driver assistive systems.

US 2008/0311983 A1 describes a motor vehicle with an oscillation unit integrated in a seat of the motor vehicle, wherein the oscillation unit is actuated in order to provide haptic feedback to the corresponding passenger while playing a video game.

It is also known from the prior art to play music in a motor vehicle for influencing the driver of the motor vehicle. DE 10 2006 015 332 A1 discloses a method for operating a motor vehicle which has such a seat and an oscillation unit integrated in the seat and a sound system, corresponding music being played back depending on a movement profile of a user of the motor vehicle and the oscillation unit being actuated, for example, to cheer up the user.

DE 10 2012 013 549 A1 proposes that, if tiredness or inattentiveness of the driver of the motor vehicle is detected, the playing of music and/or a massage function that can be manually selected by the driver are offered to the driver, in order to counteract the fatigue or inattention.

A disadvantage of such methods or motor vehicles is in particular that they are inadequate for the intended effect on the passengers.

The present invention therefore addresses the problem of providing improved or at least alternative embodiments of a method for operating a motor vehicle and of such a motor vehicle, which are characterized in particular by improved comfort and/or improved assistance systems.

The present invention is based on the general concept of performing, in a motor vehicle, an acoustic sound reproduction depending on a passenger state of a passenger of the motor vehicle and to make this sound reproduction additionally noticeable by the passenger by transmitting oscillations to the body of the passenger. Thus, with the method according to the invention, both the sound reproduction and the transmission of oscillations to the body of the passenger occur depending on the detected passenger state. As a result, the corresponding perception and effect for the passenger is intensified and/or amplified. Accordingly, assistance systems or comfort functions of the motor vehicle are enhanced. According to the inventive concept, such a motor vehicle has a seat for the passenger, which is arranged in an interior of the motor vehicle. In the seat, at least one oscillator is integrated, which serves to transmit oscillations to the body of the passenger. A sound system of the motor vehicle is used for the acoustic reproduction of sounds or for the acoustic reproduction of sound in the interior. According to the invention, a passenger state of the passenger is first determined and, depending on this passenger state, a type or a category of a sound sequence is selected. This means, in particular, that a respective category or a type of one or more sound sequences is assigned to the respectively determined passenger state, with a corresponding selection depending on the detected passenger state. The selected type of sound sequence is played back through the sound system, while at least one such oscillator is operated depending on the selected type of sound sequence and thus depending on the detected passenger state.

In the course of the determination of the passenger state, a state of mind of the passenger is preferably determined. This means that initially a state of mind of the passenger is determined and then, depending on the determined state of mind, the selection of the sound sequence and its reproduction and the operation of at least one such oscillator takes place.

The respective sound sequence can be arbitrary. In particular, the respective sound sequence can be a sequence of sounds, such as instrumental music and/or vocals.

It is advantageous if the respective oscillator, at least one such oscillator, is decoupled from the seat structure of the associated seat, such that the oscillations of the oscillator are not transmitted to the entire seat but locally to the body of the passenger. This allows a local generation and thus a local transmission of oscillations to the body of the passenger and prevents, in particular, that the oscillations are transmitted to other components of the motor vehicle. The decoupling of the oscillator from the seat structure, in particular from a padding of the seat, takes place, for example, in that the oscillator is positioned below a spacer fabric of the seat, in particular a seat cover of the seat.

In advantageous embodiments, the actuation of the at least one oscillator takes place in sync with the playback of the sound sequence. As a result, the effect of the sound sequence on the passengers can be further strengthened and/or intensified.

According to advantageous embodiments, in particular a state of tiredness and/or a state of stress of the passenger and/or a driving behavior of a driver of the motor vehicle are determined and taken into account in the determination of the passenger state. It is also conceivable that a driving situation and/or environmental values of the motor vehicle are determined and taken into account in order to determine the passenger state. Such a driving situation is, for example, the current or determined journey time, the determination of traffic congestion conditions and the like. The ambient values of the motor vehicle include, for example, climatic data and/or lighting conditions and/or the season and/or the time of day.

Variants prove to be advantageous in which at least one vital value of the passenger is taken into account for determining the passenger state. The consideration of at least one vital value of the passenger allows a reliable determination of the passenger state, in particular the state of mind of the passenger. Such vital signs include, in particular, the pulse and/or the respiration and/or the heart rate or heart rate variability and/or blood pressure and/or the skin temperature and/or a blood sugar level. Also, such vital signs may include the weight and/or body size of the passenger. Through the pulse, the respiration and the blood pressure, for example, a stress state can be determined as a passenger state. The blood sugar value allows the determination of a feeling of hunger and/or thirst.

To determine the passenger state, at least one sensor system can be provided in the vehicle. It is also conceivable to use driving data of the vehicle to determine the passenger state. These include, for example, data of an air conditioner and/or a steering behavior of the driver. In particular, vital signs of the passenger can also be determined by means of such a sensor system. In this case, both an on-board sensor system, i.e., a sensor system permanently provided onboard the vehicle, and/or a mobile sensor system, in particular a vehicle-external sensor system, can be used. The sensor system for determining the vital signs of the passenger can be provided in particular by a mobile telephone, a smartwatch, a fitness bracelet and the like. In this case, means are provided for communication between the motor vehicle and the external sensor system, which in particular allow the transmission or evaluation of the corresponding values.

The choice of a particular type of sound sequence preferably occurs in such a way that an initial classification or categorization of different sound sequences in different types of sound sequences occurs. This is preferably done such that a plurality of stored sound sequences is analyzed and the respective sound sequence is associated with at least one such type. It is conceivable to distinguish between a passenger-relaxing type and a passenger-activating type of sound sequences.

The storing and/or analysis of such sound sequences can be done both in a vehicle-internal and vehicle-external way. In a vehicle-internal implementation, it is possible, for example, to store different sound sequences in a vehicle-internal memory and analyze and categorize them as described above. In the vehicle-external variant, the sound sequences may be in particular stored in a mobile device carried by the passenger. In this case, communication between the motor vehicle and the mobile device permits, in particular, the transmission of the sound sequences to the motor vehicle, so that the sound sequences are reproduced via the sound system and the at least one oscillator is actuated depending on the reproduced sound sequence. It is conceivable, in particular, that the classification or categorization in the different types of the sound sequences stored in the mobile device is performed in the mobile device and/or in the motor vehicle.

The choice of the type of sound sequence, its reproduction and the operation of the at least one oscillator can be made such that the determined passenger state is counteracted or that the detected passenger state is supported or strengthened.

If, for example, the passenger state of a driver of the motor vehicle is determined to be a state of fatigue or stress, the choice of the type of sound sequence as well as its reproduction and the actuation of the at least one oscillator are such that the fatigue is counteracted or stress is reduced. On the other hand, if the state of the passenger is determined to be a cheerful or happy state, this state is intensified and thus supported by the selection of the type of sound sequence, its acoustic reproduction and the operation of the at least one oscillator. It is also conceivable that if a state of tiredness of a passenger, especially a non-driving passenger, is detected, this tiredness is supported through relaxation, by choosing the appropriate type of sound sequence, its acoustic reproduction and the operation of the at least one oscillator. Such relaxation may also occur in case of a driver of the motor vehicle, during an interruption, especially during a break, in order to contribute to a better recovery of the driver.

Preferably, the passenger state is determined repeatedly, for example in a loop or at predetermined, in particular regular, time intervals, and the choice of the type of sound sequence and the operation of the at least one oscillator are adjusted according to the newly determined passenger state.

It is further preferred that, in addition to the reproduction of the selected type of sound sequence and the operation of the at least one oscillator, an optical reproduction and/or an air flow and/or the emission of scents acting on the passenger occur. It is particularly preferred in this case if the acoustic reproduction of the sound sequence, the operation of the oscillator and the optical reproduction and/or the air flow and/or the scenting take place in such a way that their effects are added or reinforced. This means that the combination takes place in such a way that, for example, a relaxation of the passenger or an activation of the passenger takes place.

The respective oscillator can, in principle, be designed in any desired form and/or transmit any oscillations to the body of the passenger. Preference is given here to embodiments in which at least one such oscillator is used to transmit oscillations to the back of the passenger and/or to a leg of the passenger.

In advantageous embodiments, at least one such oscillator is configured or at least one such oscillator is actuated such that the oscillations are sub-tonal. That is, the oscillations of the oscillator are at least not directly audible to the passenger or other passengers of the motor vehicle.

It is conceivable to design at least one such oscillator as a vibration unit. Such an oscillator thus allows the transmission of oscillations to the body of the passenger and can be used for example for a massage of the passenger.

In preferred embodiments, at least one such oscillator is used for generating structure-borne noise perceived by the passenger. Thus, the acoustic perception of sound sequence reproduced by the sound system is amplified and intensified by the structure-borne sound generated by means of the at least one oscillator.

According to an advantageous embodiment, at least one such sound sequence corresponds to an acoustic behavior of a drive device of the motor vehicle. In this way the driving experience can be intensified, especially for the driver of the motor vehicle. It is also conceivable that such a sound sequence is selected depending on the acoustic behavior of the drive device of the motor vehicle. This means that a sports mode can be present in which the perception of the acoustic behavior of the drive device of the motor vehicle is amplified or intensified by the reproduction of the sound sequence and the actuation of the at least one oscillator.

It is understood that in addition to the method according to the invention, a motor vehicle also belongs to the scope of this invention. The motor vehicle may have a control device that is configured in order to operate the motor vehicle according to the method according to the invention.

Other important features and advantages of the invention will become apparent from the dependent claims, from the drawings and from the associated figure description with reference to the drawings.

It is understood that the features mentioned above and those yet to be explained below can be used not only in the particular combination given, but also in other combinations or alone, without departing from the scope of the present invention.

Preferred embodiments of the invention are illustrated in the drawings and will be described in more detail in the following description, wherein like reference numerals refer to the same or similar or functionally identical components.

BRIEF DESCRIPTION OF THE DRAWINGS

FIG. 1 shows a greatly simplified, sketch-like interior representation of a motor vehicle, FIG. 2 shows a spatial, partially transparent view of a first part of a seat of the motor vehicle, FIG. 3 shows a spatial, partially transparent view of a second part of the seat, and FIG. 4 shows a diagram for explaining the method according to the invention.

DETAILED DESCRIPTION OF THE DRAWINGS

In FIG. 1, a motor vehicle 1 with an interior 2 is shown. In the interior 2, at least one seat 3 is arranged for a passenger 4, wherein in FIG. 1, two such seats can be seen. On the front seat 3 in the direction of travel, a driver 5 can be seen as passenger 4 and on the rear seat an occupant 6 as passenger 4. In the respective seat 3, a plurality of oscillators 7 are integrated, wherein the respective oscillator 7 serves to transmit oscillations to the body of the associated passenger 4. The respective oscillator 7 can be designed as an oscillation unit 8 for transmitting oscillations to the body of the passenger 4 or as a sound generator 9 for generating structure-borne noise in the body of the passenger 4. The respective oscillator 7 is designed and/or operated in such a way that it generates sub-tonal, i.e., inaudible, oscillations.

FIGS. 2 and 3 show different views of such a seat 3, wherein in FIG. 2, the seat 3 is in the region of a backrest 10 and in FIG. 3, the seat 3 is in the region of a seat cushion 11. In FIGS. 2 and 3, the seat 3 is transparent in order to make the number and positions of the oscillators 7 more readily recognizable. From FIG. 2 it is apparent that in the respective backrest 10, two such oscillators 7 are arranged, which are positioned approximately at the same height so that they each locally transmit oscillations to the body of the passenger 4 between the shoulder and pelvis. From FIG. 3 it is apparent that four such oscillators 7 are arranged uniformly in the seat cushion 11, such that the respective oscillator 7 is arranged in the corner of a virtual, not shown quadrangle. With the oscillator 7 arranged in the seat cushion 11, oscillations can thus be transmitted to the thighs of the passenger 4.

According to FIG. 1, the motor vehicle 1 also has a sound system 12, which has a plurality of speakers 13, with which in the interior 2 an acoustic sound reproduction can occur. Optical reproduction devices 14, such as a screen 15, are also provided to the passenger 6, wherein in the example shown, one of the display devices 14 is integrated in the front seat 3 and the other display device 14 is mounted on a roof 16 of the motor vehicle 1. The display device 14 attached to the roof 16 is hereby pivotable. The sound system 12, in particular the loudspeakers 13, the oscillators 7 and the optical display devices 14 are communicatively connected to a control device 17 of the motor vehicle 1, such that the control device 17 can control them in particular.

The inventive method will be described below with reference to FIG. 4 in a simplified way. In a first step 17, the determination and detection of values which allow the determination of a passenger state 18 of such a passenger 4 in the second method step 19 takes place. These values include, in particular, vital values of the passenger 4, which are detected, for example, by a mobile device 20 carried by the passenger 4 (cf. FIG. 1), in particular by means of a mobile phone 21 and/or a fitness band 22. It is also conceivable to equip the motor vehicle 1 with corresponding sensors (not shown) which allow the determination of the vital signs. In particular, these comprise the pulse, the breathing, the heart rate or heart rate variability, blood pressure, skin temperature, and blood glucose levels. The size and weight of the passenger 4 can be determined by means of suitable sensors, not shown, which are in particular integrated in the seat 3. A driving situation, for example the duration of the journey or the duration of the journey, traffic jam situations and the like and/or environmental values of the vehicle 1, such as the current light and weather conditions, the hour of day and season and the like belong to these values, which may be detected by vehicle-internal sensors or means. If such a mobile device 20 is used, a communication interface 23 may permit communication between the mobile device 20 and the control device 17, in order in particular to transmit the values to the motor vehicle 1.

In the second method step 19, taking into account the values detected in the first step 17, the determination of the passenger state 18 takes place. It can be distinguished between different such passenger states 18. That is, the passenger 4 is assigned such a passenger state 18 depending on the detected values. In the example shown, three such passenger states 18 can be seen. These may include, for example, a tiredness state 24 in which the passenger 4 is tired, a stress state 25 in which the passenger 4 is stressed, and a cheerful mood state 26, in which the passenger 4 is cheerful. Depending on the determined values, it is thus determined in the second step 19 whether the passenger 4 is tired, stressed or cheerful. The determined passenger state 18 is used in a subsequent third step 27 to select a type 28 of a sound sequence 29. The respective type 28 may also be referred to as a category 28. At least one such sound sequence 29 is assigned to the respective type 28, wherein in the example shown, four such sound sequences 29 are assigned to the respective type 28 purely by way of example. The respective sound sequence 29 may in this case be music in particular. The respective sound sequence 29 can be stored in a vehicle-internal memory 30 or on the mobile device 20, in particular on the mobile phone 21, of the passenger 4. The assignment of the respective sound sequence 29 to such a type 28 can be carried out in a preceding method step, an analysis of the sound sequences 29 being carried out for this purpose. It is also conceivable that the respective sound sequence 29 is otherwise already associated with such a type 28. In the example shown, three such types 28 are provided, purely illustratively, namely an active type 30 activating the passengers 4, a more relaxing relaxation type 31 for the passengers 4, and a cheerfulness type 32 cheering the passenger 4. The sound sequences 29 of the active type 30 lead to an activation of the passenger 4, while the sound sequences 29 of the relaxation type 31 lead to a relaxation of the passenger 4. The sound sequences 29 of the cheerfulness type 32 lead to an increasing cheerfulness of the passenger 4. In method step 27, the selection of such a sound sequence 29 of such a type 28 thus takes place as a function of the passenger state 18 determined in step 19. If, for example, the tiredness state 24 is detected in the passenger 4, then a sound sequence 29 of type 28 associated to this passenger state 18, in particular the active type 30, is selected. Similarly, when determining a state of stress 25, such a sound sequence 29 of the type 28 associated with the stress state 25 is here selected, for example, of the relaxation type 31. When a state of cheerfulness 26 is determined, such a sound sequence 29 from the associated type 28, here, for example, the cheerfulness type 32, is selected. In the following fourth step 33, an acoustic reproduction of the selected sound sequence 29 takes place via the loudspeakers 13 of the sound system 12. Thus, if the state of tiredness 24 is determined, for example, such a sound sequence 29 of the active type 30 is selected to activate the passenger 4 and thus counteract the fatigue. If, on the other hand, a stress state 25 is determined, then, for example, such a sound sequence 29 of the relaxation type 31 is selected and reproduced via the sound system 12 in order to relax the passenger 4 and thus counteract the stress state 25. If the state of cheerfulness 26 is determined, for example such a sound sequence 29 of the assigned cheerfulness type 32 is selected and reproduced acoustically via the sound system 12 in order to support or further increase the state of merriment 26 of the passenger.

In step 33, an actuation of at least one oscillator 7 further takes place, preferably of all oscillators 7, of the seat 3 associated to passenger 4 depending on the selected type 28 of the sound sequence 29 and thus depending on passenger state 18 and from the acoustically reproduced sound sequence 29 via the sound system 12. The acoustic perception of the sound sequence 29 by the passenger 4 is thus amplified or supported by means of the at least one oscillator 7. If such an oscillator 7 is configured as a vibration unit 8, then this supporting effect is of a haptic type. If such an oscillator 7 is designed as a sound generator 9 for generating structure-borne noise in the body of the passenger 4, then in addition to the acoustic perception via the sound system 12, an amplification by structure-borne noise ensues.

With the motor vehicle 1 according to the invention and with the method of the invention thus an improvement of comfort functions for the passenger 4, in particular for the driver 5, for example by the support of the cheerfulness, by the reduction of the stress and the like, can be achieved. In addition, assistance systems can be further improved and supported, in which, for example, when detecting a state of tiredness 24, this is counteracted by appropriate measures.

It is conceivable to at least partially repeat the steps 17, 19, 27, 33 explained in FIG. 4 in order to be able to react correspondingly to changes in the passenger state 18. For this purpose, the method can return to the first step 17 after performing the fourth step 33.

Such a sound sequence 29 can in this case correspond to the acoustic behavior of a drive device 34, for example, of an internal combustion engine 35 of the motor vehicle 1, or simulate this behavior. This sound sequence 29 can for example be a sound sequence 29 of the cheerfulness type 32 and/or the active type 30. It is also conceivable to provide another type 28, not shown, for example, to provide a sports type to which the sound sequence 29 is assigned and which is selected in determining a corresponding passenger state 18 of the driver 5, for example in the presence of a sporty driving style of the driver 5. It is also conceivable to select such a sound sequence 29 depending on the acoustic behavior of the drive device 34.

The method according to the invention can be carried out separately for each passenger 4 of the motor vehicle 1. It is also conceivable to perform the method depending on several passengers 4.

An amplification of the effect on the passenger 4 produced by the acoustic reproduction of the sound sequence 29 and the actuation of the at least one oscillator 7 can be effected by an optical reproduction by at least one of the optical reproduction devices 14, preferably acting on the passenger 6. This means that the optical reproduction depends on the determined passenger state 18. Furthermore, an air flow and/or scenting may be applied to the passenger 4 additionally depending on the detected passenger state 18 in order to enhance or intensify the effect achieved.

The invention claimed is:

1. A method for operating a motor vehicle, wherein the motor vehicle includes a seat disposed in an interior of the motor vehicle for a passenger, a sound system for acoustic sound reproduction in the interior, and an oscillator integrated in the seat for transmitting oscillations to a body of the passenger, comprising the steps of:
   determining of a passenger state of the passenger;
   selecting a type of a sound sequence that is associated with the passenger state;
   reproducing the selected type of the sound sequence via the sound system; and
   activating the oscillator depending on the selected type of the sound sequence.

2. The method for operating the motor vehicle according to claim 1, wherein for the determining of the passenger state of the passenger, a state of mind of the passenger is determined and taken into account.

3. The method for operating the motor vehicle according to claim 2, wherein the state of mind is a state of fatigue or a stress condition or a driving behavior.

4. The method for operating the motor vehicle according to claim 1, wherein for the determining of the passenger state of the passenger, a driving situation or an environmental value of the motor vehicle are determined and taken into account.

5. The method for operating the motor vehicle according to claim 1, wherein for the determining of the passenger state of the passenger, a vital value of the passenger is determined and taken into account.

6. The method for operating the motor vehicle according to claim 5, wherein the vital value is a pulse or a breathing of the passenger.

7. The method for operating the motor vehicle according to claim 1 further comprising the step of analyzing a plurality of stored sound sequences to select the type of the sound sequence.

8. The method for operating the motor vehicle according to claim 1 wherein the selecting, the reproducing, and the activating are performed such that the determined passenger state is intensified.

9. The method for operating the motor vehicle according to claim 1 further comprising the step of providing an optical reproduction or an air flow or a scenting acting on the passenger, wherein the providing depends on the determined passenger state.

10. The method for operating the motor vehicle according to claim 1, wherein the oscillator generates sub-tonal oscillations.

11. The method for operating the motor vehicle according to claim 1, wherein the oscillator generates structure-borne noise in the passenger.

12. The method for operating the motor vehicle according to claim 1, wherein the selected type of sound sequence also depends on a current acoustic behavior of a drive device of the motor vehicle.

13. A motor vehicle, comprising:
   a seat disposed in an interior of the motor vehicle for a passenger;
   a sound system for acoustic sound reproduction in the interior;
   an oscillator integrated in the seat for transmitting oscillations to a body of the passenger; and
   a control device, wherein the control device is configured to perform the method according to claim 1.

* * * * *